United States Patent [19]

Klass et al.

[11] 3,994,780

[45] Nov. 30, 1976

[54] ANAEROBIC DIGESTION WITH LIBERATED ENZYME BIOMASS FRACTIONS

[75] Inventors: Donald L. Klass, Barrington; Sambhunath Ghosh, Homewood; John R. Conrad, Downers Grove, all of Ill.

[73] Assignee: Institute of Gas Technology, Chicago, Ill.

[22] Filed: Oct. 17, 1975

[21] Appl. No.: 623,416

[52] U.S. Cl. .................................. 195/13; 195/33; 210/3; 210/11
[51] Int. Cl.² .......................................... C12B 1/00
[58] Field of Search .................. 195/32, 27, 33, 34, 195/102, 13; 210/2, 16, 11, 3

[56] References Cited
UNITED STATES PATENTS 3,684,702  8/1972  Hartmann .............................. 210/3
3,801,499  4/1974  Luck .................................... 210/11

Primary Examiner—R. B. Penland
Attorney, Agent, or Firm—Dominik, Knechtel, Godula & Demeur

[57] ABSTRACT

An improved anaerobic digestion of organic biomass by rupturing cells of microorganisms present in a digested biomass or untreated biomass fraction undergoing digestion to obtain a treated biomass fraction having liberated indigenous enzymes in place; and contacting such treated biomass fraction with an untreated biomass fraction so the combined fractions undergo improved anaerobic digestion. The cells in the untreated biomass portion are ruptured by conventional means such as sonication, and about equal volumes of the fractions are preferably combined under conditions of conventional anaerobic digestion.

8 Claims, No Drawings

ANAEROBIC DIGESTION WITH LIBERATED ENZYME BIOMASS FRACTIONS

This invention relates to improved anaerobic digestion of biomass, and particularly relates to a method where liberated enzymes of a biomass contribute to more efficient digestion.

Various organic materials, collectively referred to as biomass, may be conventionally digested under anaerobic conditions to degrade or stabilize the organic content. In this metabolic process, gas is formed, principally carbon dioxide and methane. Anaerobic digestion occurs by the action of microorganisms on biodegradeable organic materials in the absence of oxygen. This is an old and well known process, and it is subject to continuing study by practitioners to improve the efficiency of digestion for the purpose of improved stabilization of organic materials or improved yields of the methane content in the gas production. It is particularly desirable to improve the production rate and yield of the methane for pipeline gas use, and new contributions to the art to serve this purpose have been disclosed in U.S. pending applications, Ser. Nos. 500,677 and 530,760 in the name of the same assignee as is identified in the present case. The application of the latter serial number disclosed improved separated acidification and gasification phases of anaerobic digestion; and the case of the former serial number discloses improved anaerobic digestion with shortened detention times. A further copending application in the name of the same assignee discloses improved digestion by controlled particle size of the biomass feed, Ser. No. 610,262.

It is an object of the present invention to improve the anaerobic digestion of biomass by utilizing indigenous enzyme systems, thus not requiring extraneous additions which could lead to greater expense and complexity in handling and operation. Advantages which characterize the attainment of this object include efficiency of obtaining indigenous enzymes from a biomass and using such enzymes in place without requiring any intermediate steps of isolation, purification, inoculations or the like.

Such object and its advantages are realized by the invention of the present disclosure, which consideration will lead to an appreciation of other objects and advantages. In summary, the indigenous or added microorganisms, which are associated with a given biomass, are subjected to conditions of cell rupture so enzymes of the rupture microorganisms are liberated into the biomass. Such liberation of indigenous enzymes can occur before, during or after anaerobic digestion of the untreated biomass which can now be considered as a treated biomass with the liberated indigenous enzymes. Such a fraction of treated biomass is then contacted with a fraction of untreated biomass to markedly improved the process of anaerobic digestion in that organics are degraded or stabilized with consequent high gas productions, including increased yields of desired methane.

The term "biomass" relates to all types of organic feeds such as sludge, animal waste, agricultural waste, trees, grasses, algae, water plants, various conditions of organic refuse or municipal waste, and various combinations thereof, including microorganisms which are enriched in the digester at the expense of the feed and are removed in the digester effluent.

The cells of the microorganisms in the untreated biomass fraction, digested or undigested, are ruptured by any one of conventional means including sonication, mechanical cell rupture by means such as shearing an untreated biomass fraction or forcing the biomass fraction through orifices dimensioned relative to the cells to rupture same or by still other mechanical cell rupture means. An attractive procedure is also provided in the art in accordance with the teachings of the present invention in that pressurization-pressure release may be used to rupture the cells. This provides impressing high pressure gradients on the untreated biomass fraction and then suddenly releasing or reducing such pressure gradients to thereby cause cell rupture. Other examples of enzyme liberation techniques are shown, for example, in U.S. Pat. No. 3,809,615. A biomass after liberation of such indigenous enzymes is referred to herein as treated biomass.

A population of microorganisms associated with a given biomass fraction expectedly contain beneficial enzyme systems effective to facilitate digestion or degrading of the particular organics present in such biomass fraction. Such enzymes may be any one or combination of amylases, proteases, or specific enzymes such as glucose oxidase, cellulase, invertase, pectinase, and the like. Microorganisms with beneficial enzymes are commonly harbored in a digester, including cellulolytic bacteria, actinomyces and fungi.

The invention has particular advantage in the improvement of anaerobic digestion of organics of low biodegradeability such as the cellulosics. The specific enzyme for such a substrate is cellulase, and this indigenous enzyme is liberated, together with others, in a biomass fraction containing such cellulosics. Enzymes have been called biological catalysts and are recognized as substances having high specificity for substrates in a "lock and key" type of reaction. The catalysis operation may be any one or more of a variety of reactions such as hydrolysis, oxidation-reductions, group transfers, group removal or addition to double bond, isomerization, joining molecules through high energy bonds, and yet still other types of operations.

The advantages of the liberated indigenous enzymes obviates the necessity for more complex conventional approaches to improving digestibility of low biodegradeable materials such as cellulosics. Some of these cumbersome conventional approaches require application of external chemicals at higher cost with concomitant residue disposal problem associated with the added chemicals.

In the practice of the process, a biomass feed may be diverted to an enzyme liberation zone, and the treated biomass fraction may then be moved to the digester zone. In the alternative, the biomass feed may first be delivered to the digester zone and a portion of the untreated digested biomass fraction may then be diverted to the enzyme liberation zone, followed by subsequent return to the digester zone. In another practice, a portion of the untreated biomass fraction can be routed to an enzyme liberation zone, and the treated biomass fraction from this zone can be moved to an enzymatic reactor zone where the treated biomass fraction, with liberated enzymes, is contacted with untreated biomass fraction prior to digestion. The mixture of treated and untreated fractions may then be moved from the enzymatic reactor zone to the digester zone where a portion is again routed to the enzyme liberation zone for recycling. Stabilized products are removed from the digester zone in the usual way.

In yet another practice, the digester process can be separated into acidification and gasification phases as disclosed in copending application Ser. No. 530,760; and an enzyme liberation zone can be separated from said two phases. Acidified untreated biomass feed can be routed to the enzyme liberation zone and the treated biomass from this zone can then be moved to the gasification zone. A portion from the gasification phase can be returned to the enzyme liberation zone for recycling to the gasification phase; or for recycling to the acidification phase.

In a presently contemplated preferred practice, untreated biomass from a digester zone is separated into a liquid effluent substantially free of solid debris. The liquid effluent contains the dispersed indigenous liberated enzymes, following earlier rupture of the cell, which can occur before, during, or after digestion. Such liquid effluent with dispersed liberated enzyme is then selectively recycled to the digestion zone, or to the separated gasification and acidification phases of a two stage digestion process.

It is therefore seen that an untreated biomass is treated in an enzyme liberation zone to obtain a treated biomass, digested or undigested. The beneficial enzymes are retained in the treated biomass when delivered to a new substrate of untreated biomass, or when the treated biomass is subsequently digested. The improved digestive system results in an improved production rate and yield of highly desired methane which can be collected for pipe line gas use.

The following examples are now presented to illustrate various embodiments of the invention, but it should be understood that such examples are not intended to represent exclusive embodiments of the invention.

EXAMPLE I

SLUDGE DIGESTER WITH LIBERATED ENZYMES

A high-rate municipal sludge digester operating at 95° F, a loading of 0.14 lb VS/CF day, and a residence time of 14 days provides a solids destruction efficiency of 33%, a yield of 2.4 CF methane/lb VS added, and a product gas containing 65% $CH_4$-35% $CO_2$. One-half of the liquid effluent from this digester is sonicated for 2 minutes at 25,000 cycles/second, and cycled back to the digester. The resulting gas yield increases to 4.0 CF methane/lb VS added at residence times of 10 days.

EXAMPLE II

EFFECT OF ENZYME LIBERATION ON DIGESTION

A biomass consisting of synthetic urban refuse and primary-activated sludge is digested under the following conditions:

| Digester: | 10 liters total volume (cylindrical) |
| --- | --- |
| | 6 liters liquid volume |
| | 180-rpm continuous mixing |
| Feed: | 56 wt % synthetic urban refuse, fiberized |
| | 44 wt % Indianapolis primary-activated sludge |
| Temperature: | 60° C |
| Detention: | 12 days |
| Loading: | 0.2 lb VS/CF-day 22g refuse in 500ml total feed/day; daily feeding |

The methane content, gas yield and gas production is measured in a first run of a single pass through the digester with no enzyme liberation.

The enzymes are liberated in a second run by high speed agitation of 500 ml of effluent in a Waring blender equipped with steel blades for 20 minutes, followed by centrifugation. A 300 ml sample of the clear supernatant liquid is added to fresh feed to bring the volume to 500 ml and the combined fractions are then fed to a digester. Alternatively, 300 ml of the clear supernatant liquid may be slurried with 22g of refuse, soaked overnight in an open container, and then mixed with sludge to 500 ml and fed to a digester.

In the third run, the enzymes are liberated by sonication of 500 ml of effluent at 80 kilohertz in a 50-watt Ultramet Sonic Cleaner (Model 75-1960-115) for 30 minutes, followed by centrifuging. A 300 ml sample of clear supernatant liquid is added to fresh feed to bring the volume to 500 ml and the combined fractions are then fed to the digester. The results are shown in the following table.

| | Run No. 1 | Run No. 2 | Run No. 3 |
| --- | --- | --- | --- |
| Methane Content, mol % | 61.0 | 46.2 | 60.7 |
| Total Gas Yield, SCF/lb VS added | 0.66 | 5.92 | 2.58 |
| Gas Production Rate, 1/day | 0.83 | 4.26 | 3.52 |

The gas yield and production rate of the treated biomass fractions in Runs Nos. 2 and 3, with liberated enzymes, are far greater than No. 1 where no enzyme liberation occurs in the untreated fraction. Such increased yield and production rate is characteristic of methane, although the methane content is substantially unchanged because of increased production of other components, particularly carbon dioxide.

The claims of the invention are now presented and the terms of such claims may be further understood by reference to the language of the preceding specifications.

What is claimed is:

1. A process of improved anaerobic digestion of biomass which includes,
    rupturing cells of microorganisms growing on the anaerobically digested biomass fraction to thereby obtain a treated biomass fraction having liberated, indigenous enzymes,
    contacting said treated liberated enzyme biomass fraction with an untreated biomass fraction so that the liberated enzymes in the treated fraction liberate indigenous enzymes in the untreated fraction, and
    anaerobically digesting said combined biomass fractions to increase methane yield and production rate.

2. A process of improved anaerobic digestion which includes the steps of claim 1 wherein liquid effluent is separated from the debris in said treated biomass fraction, and said separated liquid effluent, with liberated enzymes, is recycled to contact the untreated biomass fraction.

3. A process of improved anaerobic digestion which includes the steps of claim 1 above wherein the cells are ruptured in a biomass containing low biodegradeable cellulose, and said treated cellulosic biomass fraction is contacted with an untreated biomass fraction containing low biodegradeable cellulose.

4. A process of improved anaerobic digestion which includes the steps of claim 1 above wherein said cells are ruptured by sonicating the untreated biomass fraction for at least about 1 minute and at about at least 25,000 cycles per second.

5. A process of improved anaerobic digestion which includes the steps of claim 1 above wherein the cells in the untreated biomass portion are ruptured by impressing substantial pressure gradients on the untreated biomass portion, and then instantly releasing said pressure gradients.

6. A process of improved anaerobic digestion which includes the steps of claim 1 above wherein the cells in said untreated biomass fraction are ruptured by extruding the untreated biomass faction through orifices dimensioned relative to said cells to cause said cells to rupture.

7. A process of improved anaerobic digestion which includes the steps of claim 1 above wherein said cells in the untreated biomass fraction are ruptured by rapidly shearing said untreated biomass fraction.

8. A process of improved anaerobic digestion which includes the steps of claim 1 above wherein about equal volumes of treated and untreated biomass fractions are contacted.

* * * * *